US005760087A

United States Patent [19]

Patoiseau et al.

[11] Patent Number: 5,760,087

[45] Date of Patent: Jun. 2, 1998

[54] GLYCYLANILIDE DERIVATIVES, THEIR PREPARATION AND THEIR APPLICATION IN THERAPY

[75] Inventors: Jean-Francois Patoiseau, Castres; Jean-Marie Autin, Labruguiere; André Delhon; Philippe Oms, both of Castres, all of France

[73] Assignee: Pierre Fabre Medicament, Boulogne, France

[21] Appl. No.: 875,191

[22] PCT Filed: Jan. 18, 1996

[86] PCT No.: PCT/FR96/00081

§ 371 Date: Jul. 17, 1997

§ 102(e) Date: Jul. 17, 1997

[87] PCT Pub. No.: WO96/22279

PCT Pub. Date: Jul. 25, 1996

[30] Foreign Application Priority Data

Jan. 19, 1995 [FR] France .................................. 95 00577

[51] Int. Cl.$^6$ .................................................... A01N 37/18

[52] U.S. Cl. .......................... 514/626; 564/190; 564/191; 564/195

[58] Field of Search .................................... 564/190, 191, 564/195; 514/626

[56] References Cited

FOREIGN PATENT DOCUMENTS

| | | |
|---|---|---|
| 0415413 | 3/1991 | European Pat. Off. . |
| 0559898 | 9/1993 | European Pat. Off. . |
| 0587430 | 3/1994 | European Pat. Off. . |

*Primary Examiner*—Terressa Mosley

*Attorney, Agent, or Firm*—Rockey, Milnamow & Katz, Ltd.

[57] ABSTRACT

The invention relates to new derivatives of glycylanilides having general formula (I), wherein, particularly, $R_1$, $R_3$, $R_4$, $R_8$, $R_9$ represent $CH_3$; $R_2$, $R_5$, $R_6$, $R_7$ represent H; $R_{10}$ represents $C_{12}H_{25}$ and A is a sulfur atom. It also relates to the preparation process and the pharmaceutical compositions comprising as active principle at least one of said compounds, as well as the utilization of said derivatives for the fabrication of drugs intended to the treatment of hypercholesterolemy or atherosclerosis.

(I)

HO R1 R2 R3 R4 NH O R5 R6 R7 N O A R10 R9 R8

5 Claims, No Drawings

GLYCYLANILIDE DERIVATIVES, THEIR PREPARATION AND THEIR APPLICATION IN THERAPY

The present invention relates to new glycylanilide derivatives, to their preparation and to their application in human therapy. It also relates to the use of these derivatives for the manufacture of medicaments intended for the treatment of hypercholesterolemia or atherosclerosis.

Dietary cholesterol is absorbed in the form of free cholesterol by intestinal cells and esterified by the enzyme ACAT (acyl-CoA: cholesterol O-acyltransferase) in the serum. The inhibition of ACAT prevents the intestinal absorption and the accumulation of cholesterol in the arterial tissue. In addition, low density lipoproteins (LDL) are, after oxidation, taken up by the scavenger receptors and lead to the formation of the foam cell, the site of initiation of the atheromatous plaque (D. STEINBERG et al. England. J. Med. 320, 915–924, 1989).

The subject of the present invention is directed towards obtaining new hypocholesterolemic and antioxidant derivatives capable of acting both on the quality and the amount of the LDL, with the object of reducing their atherogenic potential and their long-term deleterious effect on the vascular wall.

The compounds of the present invention correspond to the general formula I.

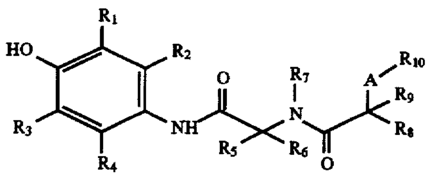

in which $R_1$, $R_2$, $R_3$, $R_4$ and $R_7$, which may be identical or different, represent, independently of one another, hydrogen or a linear or branched $C_1$–$C_4$ alkyl radical.

$R_5$, $R_6$, $R_8$ and $R_9$, which may be identical or different, represent, independently of one another, hydrogen, a linear or branched $C_1$–$C_4$ alkyl radical or an optionally substituted phenyl radical.

$R_{10}$ represents a linear or branched $C_3$–$C_{16}$ alkyl radical.

A represents a sulfur atom or a methylene group.

Since the compounds of general formula I can possess asymmetric centers, the present invention covers all the stereoisomers and mixtures thereof.

The compounds of general formula I may be prepared according to the following method (Scheme 1).

Step 1

Treatment of an Aniline With an Amino Acid Protected on the Amine Function

The protective group can be the t-butyloxycarbonyl (Boc) group.

The coupling with aniline can be accomplished by treatment with ethyl chloroformate in dimethylformamide in the presence of triethylamine.

The deprotection can be accomplished in a medium comprising 6N hydrochloric acid in methanol. The compound II is thereby obtained.

Step 2a

Treatment of the compound II obtained in step 1 with an acid chloride III to obtain the compounds I in which A=$CH_2$, or with an α-halogenated acid chloride, and then with a thiol $R_{10}SH$ in a sodium/ethanol medium or in a medium comprising potassium tert-butylate in tert-butanol, to obtain the compounds I in which A=sulfur.

Step 2b

Treatment of the compound II with an acid chloride IV in ethyl acetat in the presence of triethylamine to obtain compounds of formula I in which A is a sulfur atom or a methylene group.

SCHEME 1

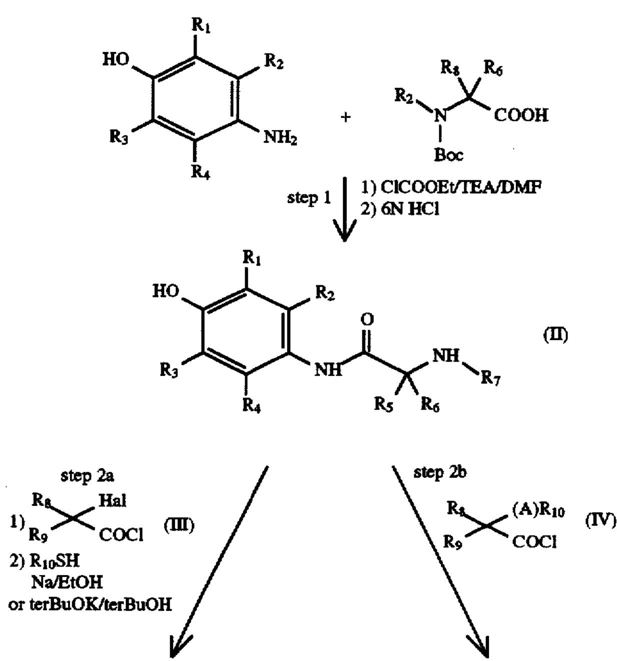

-continued

SCHEME 1

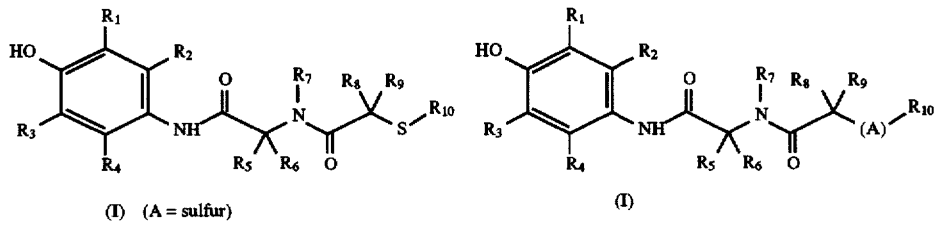

The compounds of general formula I can be used for the preparation of pharmaceutical compositions or medicaments intended for the treatment of diseases such as hypercholesterolemia or atherosclerosis.

A better understanding of the invention may be gained from the nonlimiting examples which follow, and which constitute advantageous embodiments of the process according to the invention.

EXAMPLE 1

N-(2-n-dodecylthio)propionamido-2',3',5'-trimethyl-4'-hydroxyglycylanilide 1.

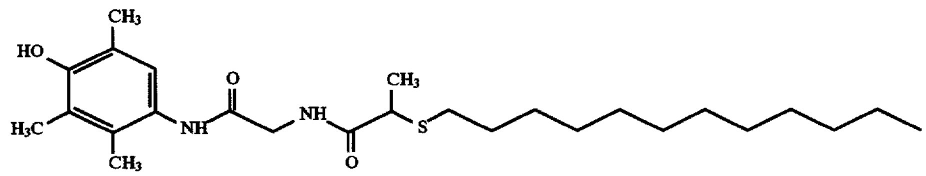

a) N-tert-butoxycarbonyl-2',3',5'-trimethyl-4'-hydroxyglycylanilide 1a

A solution of ethyl chloroformate (0.96 ml; 0.01 mol) in $CH_2Cl_2$ (5 ml) is added dropwise to an ice-cold solution of boc-glycine (1.75 g; 0.01 mol) and N-methylmorpholine (2.19 mol; 0.02 mol) in methylene chloride (10 ml). After 20 minutes of contact at 0° C., 2,3,6-trimethyl-4-aminophenol hydrochloride (1.88 g; 0.01 mol) in $CH_2Cl_2$ (40 ml) is added under nitrogen. The reaction mixture is then stirred for 24 hours at room temperature and evaporated under vacuum. The residue is taken up with water and extracted with ethyl acetate. The organic phase is washed with N hydrochloric acid and with water, then dried ($Na_2SO_4$) and concentrated under vacuum. The residue is purified by flash chromatography. 1.42 g of crystals 1a are obtained.

M.p.=208° C.

TLC: Merck silica gel 60F254. Rf=0.54 (AcOEt)

b) 2',3',5'-trimethyl-4'-hydroxyglycylanilide 1b 12 ml of 6N hydrochloric acid are added to the compound 1a (3.08 g; 0.01 mol) in methanol (100 ml). The solution is stirred at 60° C. for 5 hours and then concentrated under vacuum. The solid is taken up with water, adjusted to pH 9 by adding N sodium hydroxide and extracted 3 times with ethyl acetate. The combined organic phases are washed with water, dried ($Na_2SO_4$) and evaporated under vacuum. Treatment with hexane to form a paste yields, after filtration, the compound 1b (1.89 g).

M.p.=177° C.

TLC: Merck silica gel 60F254. Rf=0.30 ($CH_2Cl_2$/MeOH 50:50)

c) N-(α-bromopropionamido)-2',3',5'-trimethyl-4'-hydroxyglycylanilide 1c

A solution of derivative 1b (2.08 g; 0.01 mol) in ethyl acetate (35 ml) is treated with triethylamine (1.67 ml; 0.012 mol) and then, dropwise, with α-bromopropionyl bromide in ethyl acetate (15 ml) at room temperature. After stirring for one hour, the reaction medium is washed with water, dried ($Na_2SO_4$) and concentrated under vacuum. The solid is taken up with hexane, filtered and dried to give the compound 1c (2.89 g).

M.p.=178° C.

TLC: Merck silica gel 60F254. Rf=0.48 ($CH_2Cl_2$/MeOH 90:10).

d) N-(2-n-dodecylthio)propionamido-2',3',5'-trimethyl-4'-hydroxyglycylanilide 1

A mixture of sodium in a 45% dispersion in paraffin (0.63 g, 0.012 g-at.) and n-dodecanethiol (2.9 ml; 0.01 mol) is heated to 110° C. for 45 minutes. After cooling, the thiolate is dissolved in ethanol (30 ml). The derivative 1c (3.43 g; 0.01 mol) is then added and the reaction mixture is brought to reflux for 6 hours. It is evaporated under vacuum and the residual oil is extracted with methylene chloride. The organic phase is washed with N HCl, with water and with aqueous saline solution. After drying and concentration of the solution, white crystals of product 1 are obtained (3.29 g).

M.p.=109° C.

TLC: Merck silica gel 60F254. Rf=0.33 ($CH_2Cl_2$/AcOEt 70:30)

EXAMPLE 2

N-(α,α,-dimethyl)tetradecanamido-2',3',5'-trimethyl-4'-hydroxyglycylanilide

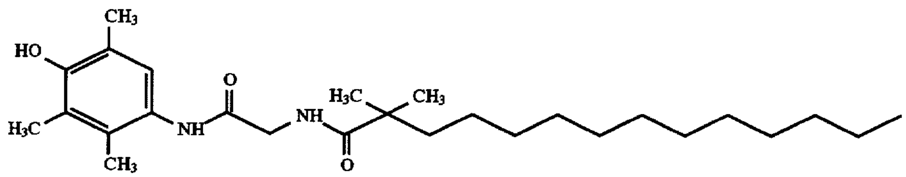

α,α-Dimethyltetradecanoyl chloride (3.3 g; 0.01 mol, prepared by the action of thionyl chloride on the corresponding acid for 3 hours under reflux of toluene) in tetrahydrofuran (40 ml) is added dropwise to a solution of 2',3',5'-trimethyl-4'-hydroxyglycylanilide (2.08 g; 0.01 mol) (prepared according to 1b) and triethylamine (3.34 ml; 0.024 ml) in DMF (20 ml). After stirring for 4 hours at room temperature, the reaction mixture is diluted with water and extracted with ethyl acetate. The organic phase is washed with N HCl and with water, then dried and concentrated under vacuum. The solid obtained is then purified by flash chromatography (3.13 g).

M.p.=162° C.

TLC: Merck silica gel 60F254. Rf=0.56 (AcOEt)

EXAMPLE 3

N-methyl-N-(α-n-dodecylthio)isobutyramido-2',3',5'-trimethyl-4'-hydroxyglycylanilide

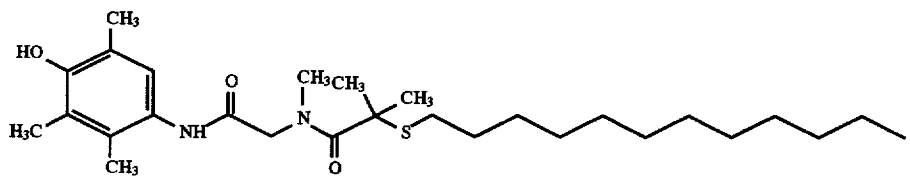

This compound was prepared according to the process described in Example 1a and 1b, using N-boc-sarcosine, followed by condensation of α-n-dodecylthioisobutyryl chloride according to Example 2.

M.p.=115° C.

TLC: Merck silica gel 60F254. Rf=0.46 (AcOEt/hexane 50:50).

EXAMPLE 4

N-(α-n-dodecylthio)butyramido-2',3',5'-trimethyl-4'-hydroxyglycylanilide

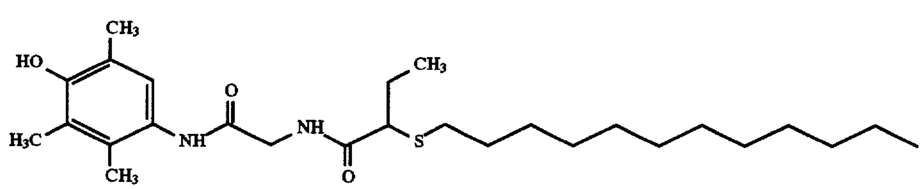

This compound was prepared according to the process described in Example 1, using 2-bromobutyryl bromide.

M.p.=115° C.

TLC: Merck silica gel 60F254. Rf=0.46 (AcOEt/hexane 50:50).

EXAMPLE 5

N-(α-n-dodecylthio)isobutyramido-2',3',5'-trimethyl-4'-hydroxyglycylanilide

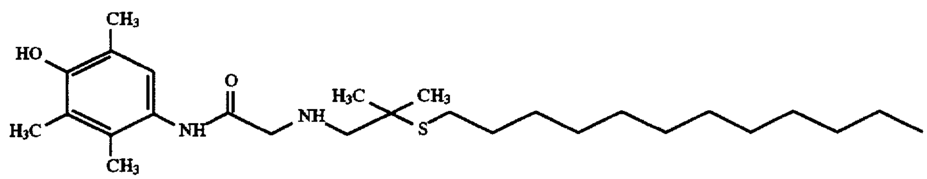

This compound was prepared according to the process described in Example 2, using α-dodecylthioisobutyryl chloride.

M.p.—113° C.

TLC: Merck silica gel 60F254. Rf=0.37 (AcOEt/hexane 50:50).

EXAMPLE 6

N-(d-n-dodecylthio)acetamido-2',3',-5'-trimethyl-4'-hydroxyglycylanilide

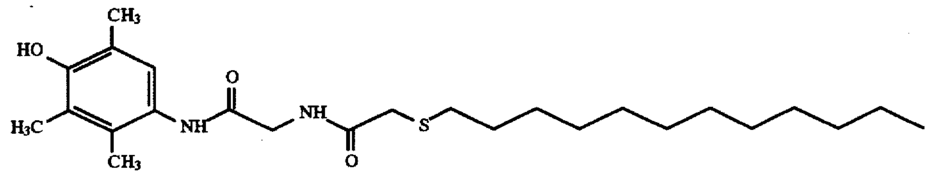

This compound was prepared according to the process described in Example 1, using chloroacetyl chloride.

M.p.=128° C.

TLC: Merck silica gel 60F254. Rf=0.50 (AcOEt).

EXAMPLE 7

N-(α-n-dodecylthio)butyramido-2-ethyl-2',3',5'-trimethyl-4'-hydroxyglycylanilide

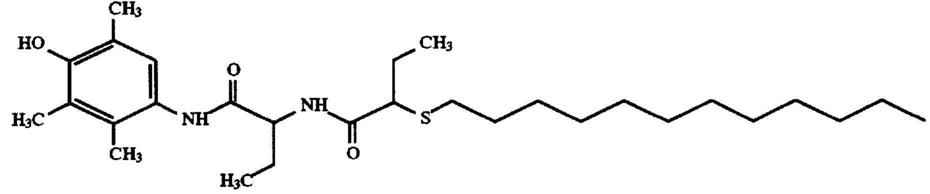

This compound was prepared according to the processes described in Examples 1a and 1b, using α-bocaminobutyric acid, followed by the processes 1c and 1d using α-bromobutyryl bromide.

M.p.=153° C.

TLC=Merck silica gel 60F254. Rf=0.54 ($CH_2Cl_2$/AcOEt 70:30).

EXAMPLE 8

N-methyl-N-(α-n-dodecylthio)propionamido-2',3',5'-trimethyl-4'-hydroxyglycylanilide

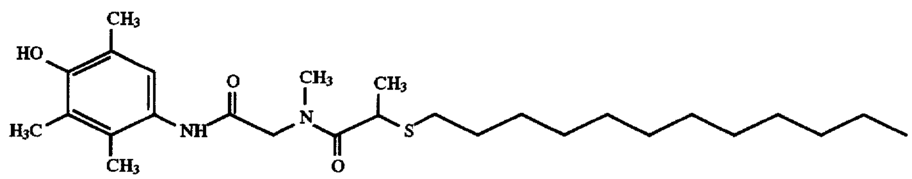

This compound was prepared according to the processes described in Examples 1a and 1b, using boc-sarcosine, followed by the processes 1c and 1d using 2-bromopropionyl bromide.

M.p.=106° C.

TLC=Merck silica gel 60F254. Rf=0.47 (AcOEt).

EXAMPLE 9

N-(α-n-dodecylthio)isobutyramido-2-n-butyl-2',3',5'-trimethyl-4'-hydroxyglycylanilide

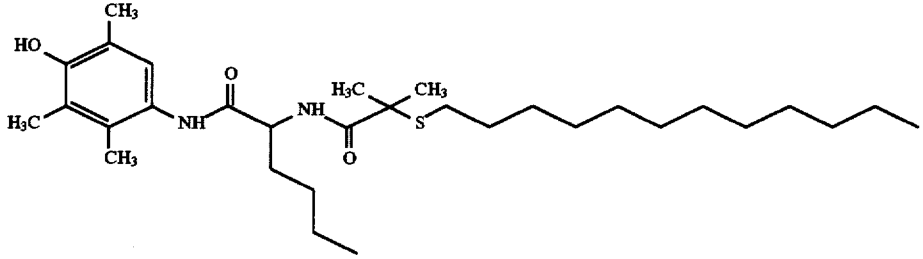

This compound was prepared according to the processes described in Examples 1a and 1b, using α-aminohexanoic acid according to the process of Example 2, using α-dodecylthioisobutyryl chloride.

M.p.=113° C.

TLC: Merck silica gel 60F254. Rf=0.40 ($CH_2Cl_2$/AcOEt 90:10).

EXAMPLE 10

N-(α-n-dodecylthio)isobutyramido-2-phenyl-2',3',5'-trimethyl-4'-hydroxyglycylanilide

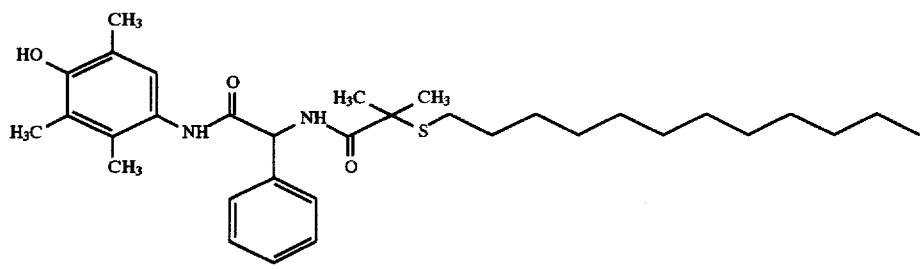

This compound was prepared according to the processes described in Examples 1a and 1b, using N-boc-phenylglycine, and then according to the process of Example 2.

M.p.=71° C.

TLC=Merck silica gel 60F54. Rf=0.35 ($CH_2Cl_2$/AcOEt 90:10).

EXAMPLE 11

N-(α-n-dodecylthio)phenylacetamido-2',3',5'-trimethyl-4'-hydroxyglycylanilide

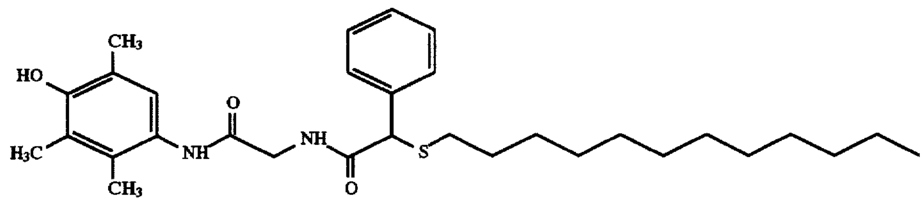

This compound was obtained according to the process described in Example 1, using α-chlorophenylacetyl chloride.

M.p.=127° C.

TLC: Merck silica gel 60F254. Rf=0.58 ($CH_2Cl_2$/AcOEt 70:30).

EXAMPLE 12

N-(α-n-dodecylthio)isobutyramido-3',5'-bis-tert-butyl-4'-hydroxyglycylanilide

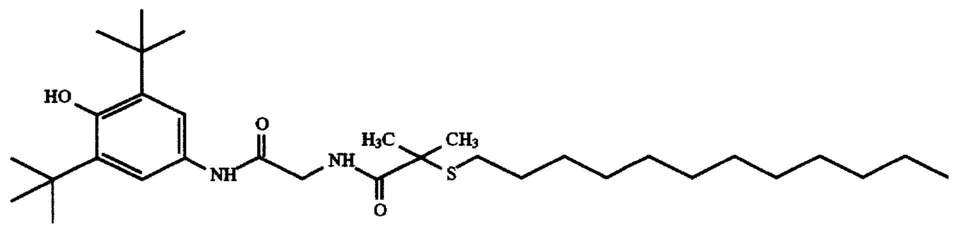

This compound was obtained according to the process described in Example 2, using 2,6-bisterbutyl-4-aminophenol.

M.p.=103° C.

TLC: Merck silica gel 60F254. Rf=0.63 (AcOEt/hexane 50:50).

EXAMPLE 13

N-(α-n-dodecylthio)propionamido-3',5'-bis-tert-butyl-4'-hydroxyglycylanilide

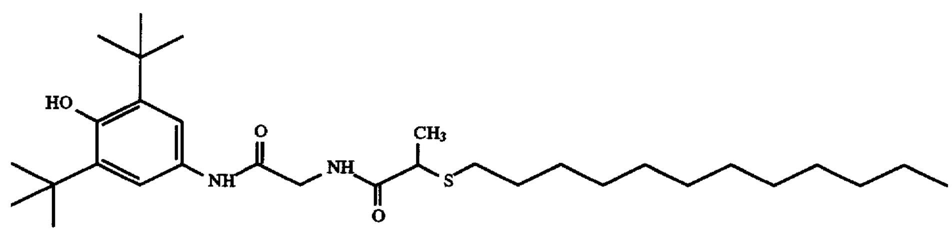

This compound was obtained according to Example 12.

M.p.—93° C.

TLC: Merck silica gel 60F254. Rf=0.38 (AcOEt/hexane 50:50).

EXAMPLE 14

N-(α-n-dodecylthio)propionamido-3'-methyl-4'-hydroxy-5'-tert-butylglycylanilide

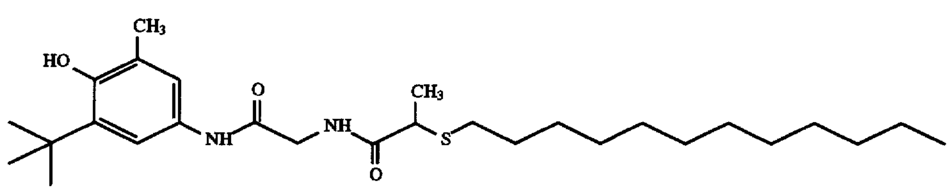

This compound was obtained according to the process described in Example 1, using 2-methyl-4-amino-6-terbutylphenol.

M.p.=84° C.

TLC: Merck silica gel 60F254. Rf=0.42 ($CH_2Cl_2$/AcOEt 70:30).

EXAMPLE 15

N-methyl-N-(α-n-dodecylthio)propionamido-3'-methyl-4'-hydroxy-5'-tert-butylglycylanilide

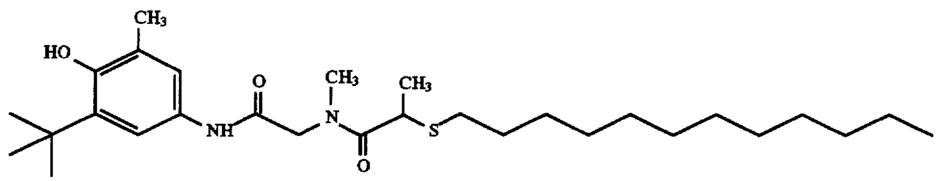

This compound was obtained according to Example 14, using N-boc-sarcosine.

M.p.=117° C.

TLC: Merck silica gel 60F254. Rf=0.28 (AcOEt/hexane 50:50).

EXAMPLE 16

N-(α-n-dodecylthio)isobutyramido-3'-methyl-4'-hydroxy-5'-tert-butylglycylanilide

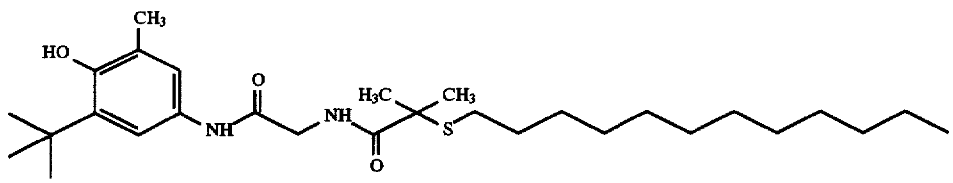

This compound was prepared according to the process described in Example 2.

M.p.=90° C.

TLC: Merck silica gel 60F254. Rf=0.38 (AcOEt/hexane 50:50).

EXAMPLE 17

N-(α-n-dodecylthio)butyramido-3'-methyl-4'-hydroxy-5'-tert-butylglycylanilide

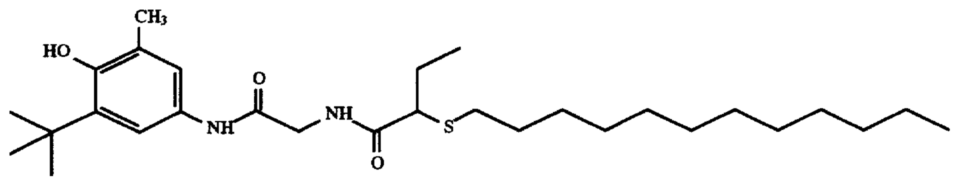

This compound was obtained according to the process described in Example 1, using 2-bromobutyryl bromide.

M.p.=125° C.

TLC: Merck silica gel 60F254. Rf=0.42 (AcOEt/hexane 50:50).

The compounds of the invention were subjected to pharmacological tests which showed their potential value in the treatment of hypercholesterolemia and of atheromatous disease.

The compounds were studied for their inhibitory effect on ACAT and hypocholesterolemic effect in rats on the one hand and for their antioxidant effect on the other hand.

1) Inhibition of ACAT

The inhibitory activity of the compounds with respect to ACAT (acyl-CoA:cholesterol O-acyltransferase enzyme) was evaluated in vitro using the technique of H. CHAUTAN et al. (Analytical Biochemistry 173, 436–439, 1988).

The activities, expressed as 50% inhibitory concentrations ($IC_{50}$), obtained on some products of the invention, are recorded, by way of example, in Table 3 below:

| Compound No. | $IC_{50}$ (μM) |
|---|---|
| 1 | 1.2 |
| 2 | 0.74 |
| 3 | 0.16 |
| 5 | 0.62 |
| 8 | 0.28 |
| CI 976 | 0.98 |
| DUP 128 | 0.09 |

2) Hypocholesterolemic Activity

Male rats (160–180 g) are subjected for 4 days to an Altromin C 1061 hypercholesterolemic diet, and concomitantly treated orally with the compounds suspended in carboxymethylcellulose at a concentration of 1%.

On day 5, the animals, fasted for 16 hours, are anesthetized with ethyl ether and exsanguinated by drawing blood at the abdominal aorta onto EDTA.

The blood is immediately centrifuged and the plasma stored at 4° C.

Plasma cholesterol is then assayed by the CHOP-PAP method (Boehringer-Mannheim Ref. 237574).

The median effective dose ($ED_{50}$) corresponds to the dose which reduces the plasma cholesterol concentration by half relative to control animals.

| Compound No. | $ED_{50}$ (mg/kg) |
|---|---|
| 1 | 1 |
| 2 | 3 |
| 3 | <2.5 |
| 5 | 2.5 |
| 8 | 4 |
| CI 976 | 7.2 |
| DUP 128 | 1.4 |

3) Antioxidant Activity a) Chemical Peroxidation

In the presence of $Fe^{3+}$ and ADP, dihydroxyfumaric acid undergoes an autoxidation which generates oxygen free radicals. The latter bring about the peroxidation of hepatic microsomal lipids.

This peroxidation, performed on rat liver microsomes, is measured according to the thiobarbituric acid technique (formation of T.BARS) as described by S. Y. H. TSE et al. (Biochemical Pharmacology, Vol. 42, No. 3, 459–464, 1991).

| Compound No. | $IC_{50}$ (μM) |
|---|---|
| 1 | 3 |
| 2 | 0.5 |
| 3 | 0.5 |
| 5 | 0.3 |
| 8 | 0.5 |
| CI 976 | >10 |
| DUP 128 | >10 |

b) Oxidation of LDL

Human LDL (Sigma L 2139) are oxidized with 4.5 μM $CuSO_4$.

After an incubation period of 6 hours, the peroxidation is evaluated by measuring the T.BARS by spectrophotometry at 532 nanometers.

| Compound No. | $IC_{50}$ (μM) |
|---|---|
| 1 | 5 |
| 2 | 1 |
| 3 | 5 |
| 5 | 3 |
| 8 | 3 |
| CI 976 | 100 |
| DUP 128 | 30 |

The compounds of the invention are hypocholesterolemic agents that inhibit ACAT and antioxidants, which can be used for the treatment of diseases such as hypercholesterolemia and atherosclerosis.

The pharmaceutical compositions can be presented in the form suitable for oral, parenteral or local administration, for example in the form of capsules, tablets, granules, hard gelatin capsules, liquid solutions, syrups or suspensions to be swallowed, and can contain the appropriate excipients.

The daily dosage can range from 10 to 2000 mg.

We claim:

1. Glycyclanilide derivatives, that correspond to the general formula I:

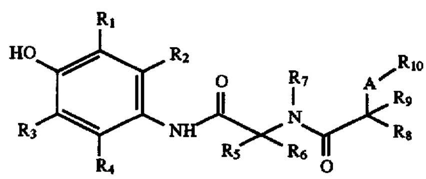

in which:

$R_1$, $R_2$, $R_3$, $R_4$ and $R_7$, which are identical or different and are selected from hydrogen or a linear or branched $C_1$–$C_4$ alkyl radical;

$R_5$, $R_6$, $R_8$ and $R_9$, which are identical or different and are selected from hydrogen, a linear or branched $C_1$–$C_4$ alkyl radical or an optionally substituted phenyl radical;

$R_{10}$ represents a linear or branched $C_3$–$C_{16}$ alkyl radical; and

A is selected from a sulfur atom or a methylene group.

2. Compounds corresponding to the general formula (I) according to claim 1, selected from the following group:

N-(2-n-dodecylthio)propionamido-2',3',5'-trimethyl-4'-hydroxyglycylanilide;

N-(α,α-dimethyl)tetradecanamido-2',3',5'-trimethyl-4'-hydroxyglycylanilide;

N-methyl-N-(α-n-dodecylthio)isobutyramido-2',3',5'-trimethyl-4'-hydroxyglycylanilide;

N-(α-n-dodecylthio)butyramido-2',3',5'-trimethyl-4'-hydroxyglycylanilide;

N-(α-n-dodecylthio)isobutyramido-2',3',5'-trimethyl-4'-hydroxyglycylanilide;

N-(α-n-dodecylthio)acetamido-2',3',5'-trimethyl-4'-hydroxyglycylanilide;

N-(α-n-dodecylthio)butyramido-2-ethyl-2',3',5'-trimethyl-4'-hydroxyglycylanilide;

N-methyl-N-(α-n-dodecylthio)propionamido-2',3',5'-trimethyl-4'-hydroxyglycylanilide;

N-(α-n-dodecylthio)isobutyramido-2-n-butyl-2',3',5'-trimethyl-4'-hydroxyglycylanilide;

N-(α-n-dodecylthio)isobutyramido-2-phenyl-2',3',5'-trimethyl-4'-hydroxyglycylanilide;

N-(α-n-dodecylthio)phenylacetamido-2',3',5'-trimethyl-4'-hydroxyglycylanilide;

N-(α-n-dodecylthio)isobutyramido-3',5'-bis-tert-butyl-4'-hydroxyglycylanilide;

N-(α-n-dodecylthio)propionamido-3',5'-bis-tert-butyl-4'-hydroxyglycylanilide;

N-(α-n-dodecylthio)propionamido-3'-methyl-4'-hydroxy-5'-tert-butylglycylanilide;

N-methyl-N-(α-n-dodecylthio)propionamido-3'-methyl-4'-hydroxy-5'-tert-butylglycylanilide;

N-(α-n-dodecylthio)isobutyramido-3'-methyl-4'-hydroxy-5'-tert-butylglycylanilide;

N-(α-n-dodecylthio)butyramido-3'-methyl-4'-hydroxy-5'-tert-butylglycylanilide.

3. Process for preparing the compound according to claim 1 wherein:

a) an aniline is treated with a Boc-amino acid in the presence of ethyl chloroformate and triethylamine in dimethylformamide and then with 6N hydrochloric acid to yield the intermediate II.

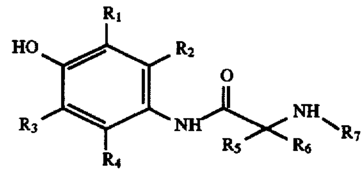

in which $R_1$, $R_2$, $R_3$, $R_4$, $R_5$, $R_6$ and $R_7$ are as defined in claim 1.

b) the intermediate II is treated with an α-halogenated acid chloride III

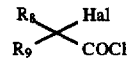

in which $R_8$ and $R_9$ are as defined in claim 1 and Hal represents chlorine or bromine, and then with a thiol $R_{10}SH$, $R_{10}$ having the same meaning as in claim 1, in a sodium/ethanol medium or in a medium comprising potassium tert-butylate in tert-butanol, to obtain the compounds I in which A=sulfur, or the intermediate II is treated with a derivative IV

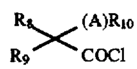

(IV)

in which $R_8$, $R_9$, $R_{10}$ and A have the same meaning as in claim 1, in ethyl acetate in the presence of triethylamine, to obtain compounds in which A is a sulfur atom or a methylene group.

4. Pharmaceutical compositions that comprise a pharmaceutically acceptable vehicle and at least one compound of general formula I according to claim 1.

5. A method for treating hypercholesterolemia or atherosclerosis by inhibiting LDL oxidation associated therewith that comprises the administration of an effective amount of at least one compound of claim 1 to a patient in need of such treatment.

* * * * *